US006984528B2

(12) United States Patent
Reppy et al.

(10) Patent No.: US 6,984,528 B2
(45) Date of Patent: Jan. 10, 2006

(54) METHOD FOR DETECTING AN ANALYTE BY FLUORESCENCE

(75) Inventors: Mary A. Reppy, Wilmington, DE (US);
Sarah A. Sporn, Wilmington, DE (US);
Charles F. Saller, San Diego, CA (US)

(73) Assignee: Analytical Biological Services Inc., Wilmington, DE (US)

( * ) Notice: Subject to any disclaimer, the term of this patent is extended or adjusted under 35 U.S.C. 154(b) by 287 days.

(21) Appl. No.: 09/811,538

(22) Filed: Mar. 20, 2001

(65) Prior Publication Data

US 2004/0110223 A1 Jun. 10, 2004

Related U.S. Application Data

(60) Provisional application No. 60/190,091, filed on Mar. 20, 2000.

(51) Int. Cl.
*G01N 33/53* (2006.01)
*G01N 21/76* (2006.01)

(52) U.S. Cl. .................. 436/829; 436/172; 436/528; 436/531; 435/7.1; 424/450; 424/417

(58) Field of Classification Search .................. 422/55, 422/57, 58, 60, 82.05, 82.06, 82.07, 82.08; 436/518, 528, 531, 535, 815, 823, 829, 172; 435/4, 6, 7.1
See application file for complete search history.

(56) References Cited

U.S. PATENT DOCUMENTS

| | | | |
|---|---|---|---|
| 4,859,538 A | | 8/1989 | Ribi |
| 5,415,999 A | * | 5/1995 | Saul et al. ................ 435/7.9 |
| 5,427,915 A | * | 6/1995 | Ribi et al. ............... 422/82.05 |
| 5,618,735 A | * | 4/1997 | Saul et al. ................ 422/60 |
| 5,622,872 A | | 4/1997 | Ribi |
| 6,001,556 A | | 12/1999 | Charych et al. |
| 6,022,748 A | * | 2/2000 | Charych et al. ........... 436/535 |
| 6,080,423 A | | 6/2000 | Charych et al. |
| 6,180,135 B1 | * | 1/2001 | Charych et al. ........... 424/450 |
| 6,183,772 B1 | | 2/2001 | Charych et al. |

FOREIGN PATENT DOCUMENTS

| | | |
|---|---|---|
| WO | WO 95/02183 A1 | 1/1995 |
| WO | WO 98/36263 A1 | 8/1998 |
| WO | WO 98/39632 A1 | 9/1998 |
| WO | WO 99/10743 A1 | 3/1999 |
| WO | WO 99/67423 A1 | 12/1999 |

OTHER PUBLICATIONS

Reichert et al., Polydiacetylene Liposomes Functionalized with Salic Acid Bind and Colorimetrically Detect Influenza Virus, J. Am. Chem. Soc., 1995, 117:829–830.*
Tetsuya Kondo et al., Biochimica et Biophysica Acta. 1124, 1992, pp. 1–6, Hydrolysis of Phospholipid Monolayers by Phospholipase D at the Oil/Water Interface Under the Control of the Potential Drop Across the Monolayer.

Miquel Pons et al., Biochimica et Biophysica Acta, 693, 1982, pp. 461–446, the Optical Activity and Circular Dichroic Spectra of Diacetylenic Phospholipid Polymers, 5.
Alok Singh et al., Journal of the American Chemical Society, 1986, 108, pp. 2785–2787, Reversible Thermochromism in Photopolymerized Phosphatidylcholine Vesicles.
Troy E. Wilson et al., Journal of the American Chemical Society, 1992, 8, pp. 2361–2364, Polydicetylene Monolayers Functionalized with Amino Acids.
Deborah H. Charych et al., Science, 1993, 261, pp. 585–588, Direct Colorimetric Detection of a Receptor–Ligand Interaction by a Polymerized Bilayer Assembly.
Anke Reichert et al., Journal of the American Chemical Society, 1995, 117, pp. 829–830, Polydiacetylene Liposomes Functionalized with Sialic Acid Bind and Colorimetrically Detect Influenza Virus.
Wayne Spevak et al., Advanced Materials, 1995, 7(1), pp. 85–89, Molecular Assemblies of Functionalized Polydiacetylenes.
John J. Pan et al., Journal of the American Chemical Society, 1997, 13, pp. 1365–1367, Molecular Recognition and Colorimetric Detection of Cholera Toxin by Poly(diacetylene) Liposomes Incorporating Gm1 Ganglioside.
D. Bloor et al., Journal of Polymer Science, 1981, 19, pp. 321–334, Spectroscopic Studies of Solutions, Suspensions, and Precipitates of Poly(1,6–di–p–toluene sulfonyloxy–2, 4–hexadiyne).
R. Warta et al., Journal of Chemical Physics, 88(1), pp. 95–99, Optical Absorption and Fluorescene Spectroscopy of Stable Diacetylene Oligomer Molecules.
J. Morgan et al., Chemical Physics Letters, 1992, 196(5), pp. 455–461, Photophysics of the Chiral Soluble Polydiacetylene Poly(9RMBU). Evidence for Emission from Short Conjugated Sequences.
Garry Rumbles et al., Journal of the Chemical Society, Faraday Transactions, 1992, 88(22), pp. 3313–3318, Surface–Induces Chromism and Enhanced Fluorescence of the Soluble Polydiacetylene, Poly(4–Butoxycarbonylmethylurethane), at a Solid/Solution Interface: An Evanescent–Wave Induced Fluorescence Study.
R. Lecuiller et al., The American Physical Society, 1998, 80(18), pp. 4068–4071, Dual Resonance Fluorescence of Polydiacetylene Chains Isolated in Their Crystalline Monomer Matrix.

(Continued)

*Primary Examiner*—Padmashri Ponnaluri
*Assistant Examiner*—My-Chau T. Tran
(74) *Attorney, Agent, or Firm*—Connolly Bove Lodge & Hutz LLP; Burton Amernick (57) ABSTRACT

Two-dimensional and three-dimensional arrays of a polydiacetylene backbone having a substrate incorporated are used in chemical sensing methods to detect the interaction of an analyte with the substrate by monitoring the change in the fluorescence of the array.

19 Claims, 5 Drawing Sheets

OTHER PUBLICATIONS

A. Yasuda et al., Chemical Physics Letters, 1993, 209(3), pp. 281–286, Flourescence Spectrum of a Blue–Phase Polydiacetylene Obtained by Probe Saturation Spectroscopy.

Sheldon Okada et al., Accounts of Chemical Research, 1998, 31, pp. 229–239, Color and Chromism of Polydiacetylene Vesicles.

Raz Jelinek et al., Chemistry & Biology, 1998, 5, pp. 619–629, Interfacial Catalysis by Phospholipases at Conjugated Lipid Vesicles Colorimetric Detection and NMR Spectroscopy.

Sofiya Kolusheva et al., Journal of the American Chemical Society, 2000, 122(5), pp. 776–780, Cation–Selective Color Sensors Composed of Ionophore–Phospholipid–Polydiacetylene Mixed Vesicles.

Sofiya Kolusheva et al., Nature Biotechnology, 2000, 18, pp. 225–227, A Colorimetric Assay for Rapid Schreening of Antimicrobial Peptides.

Sofiva Kolusheva et al., Journal of the American Chemical Society, 2001, 123, pp. 417–422, Rapid Colorimetric Detection of Antibody–Epitope Recognition at a Biomimetic Membrane Interface.

Zhanfang Ma et al., Journal of the American Chemical Society, 1998, 120, pp. 12678–12679, Colorimetric Detection of *Escherichia coli* by Polydiacetylene Vesicles Functionalized with Glycolipid.

Zhanfang Ma et al., Journal of the American Chemical Society, 2000, 16, pp. 7801–7804, Influence of the Spacer Length of Glycolipid Receptors in Polydiacetylene Vesicles on the Colorimetric Detection of *Escherichia coli*.

Quan Cheng et al., Advanced Materials, 1997, 9(6), pp. 481–483, Coupling of an Induced Fit Enzyme to Polydiacetylene Thin Films Colorimetric Detection of Glucose.

D. Tyler McQuade et al., The Journal of the American Chemical Society, 2000, 122, pp. 12389–12390, Signal Amplification of a "Turn–On" Sensor: Harvesting the Light Captured by a Conjugated Polymer.

Shirley J. Johnson et al., Langmuir 1995, 11, pp. 1257–1260, Formation of Poly(Diacetylene)Thin Films with Uniform Fluorescence.

T. E. Wilson. et al., Langmuir, 1992, 8, pp. 2588–2590, Imaging a Mono–Layer Polydiacetylene Film by Confocal Fluorescence Microscopy to Characterize the Surface etc.

M.H.P Moers. et al., Langmuir, 1994, 33, pp. 2774–2777, Confocal Fluorescence Microscopy on Red Polydiacetylene Mono–Layer as Part of a Study of Surface Topography.

W.E. Lindsell. et al., Polymer International, 1994, 33, pp. 87–92, Fluorescence of Polydiacetylene in Solution;Discussion of Correlation of Conjugation Lengths with Absorbance/Excitation Energies.

V. Bliznyuk et al., Thin Solid Films, 1994, 244, pp. 1037–1042, Cyanine Dye Layer on Diacetylene Film & Photopolymerization Sensitized by the Dye Crystals.

I.T. Dorn et al., Langmuir, 1998, 14, pp. 4836–4842, Fluorescence Microscopy on Polydiacetylene Films with Metal Chelating Headgroups; Binding of Histidine–Tagged Protein/DNA Complexes Detected by Atomic Force Microscopy (Not Fluorescence).

David G. Rhodes et al., Langmuire 1994, 10, pp. 267–275, Structure of Polymerizable Lipid Bilayers. 6, BiLayer Structure of Three Polymerizable Diacetylenic Glutamate Lipids.

David A. Frankel et al., Journal of the American Chemistry Society, 1994, 116, pp. 10057–10069, Supramolecular Assemblies of Diacetylenic Aldonamides.

B. Tieke et al. Chem. Int. Ed. Engl., 1976, 15(12), pp. 764–765, Polymerization of Tricosa–10,12–Diynoic Acid in Mulitlayers.

Anthony Huang et al., The Journal of Biological Chemistry, 255(17), pp. 8015–8018, Monoclonal Antibody Covalently Coupled with Fatty Acid.

Bernd Hupfer et al., Chemistry and Physics of Lipids, 1983 33, pp. 355–374, Liposomes from Polymerizable Phospholipds.

Wayne Spevak et al., Journal of the American Chemistry Society, 1993, 115, pp. 1146–1147 Polymerized Liposomes Containing C–Glycosides of Sialic Acid: Potent Inhibitors of Influenza Virus in Vitro Infectivity.

Greg T. Hermanson, Bioconjugate Techniques, p. 82–83, 463–465.

Reichert et al., Journal of the American Chemistry Society, 1995, 117, pp. 829–820, Polydiacetylene Liposomes Functionalized with Salic Acid Bind and Colorimetrically Detect Influenza Virus.

* cited by examiner

Figure 1. 1,4-addition photopolymerization of 1,3-diacetylenes

Figure 4. (a) poly(PDA) liposomes and (b) poly(PDA/DIC-18(5) liposomes; both heated at 70 C; excitation = 475nm Figure 5. Polymerized coated membrane (PDA/DIC-18(5)/antibody) exposed to (a) H2O and (b) *Chlamydia* E

METHOD FOR DETECTING AN ANALYTE BY FLUORESCENCE

CROSS-REFERENCE TO RELATED APPLICATION

This application claims priority from U.S. Provisional Patent Application S.N. 60/190,091 filed Mar. 20, 2000.

FEDERALLY SPONSORED RESEARCH OR DEVELOPMENT

The invention in this application was partially made with finding from the National Institutes of Health under grant award no. 2-R44-6M57154-02.

TECHNICAL FIELD

The present invention relates to a method for detecting the presence of an analyte in a sample, and more particularly, to a method involving the monitoring of the change in fluorescence. According to the present invention, an array incorporating a polydiacetylene backbone with a substrate incorporated in the array is employed.

BACKGROUND OF THE INVENTION

Figure 1:
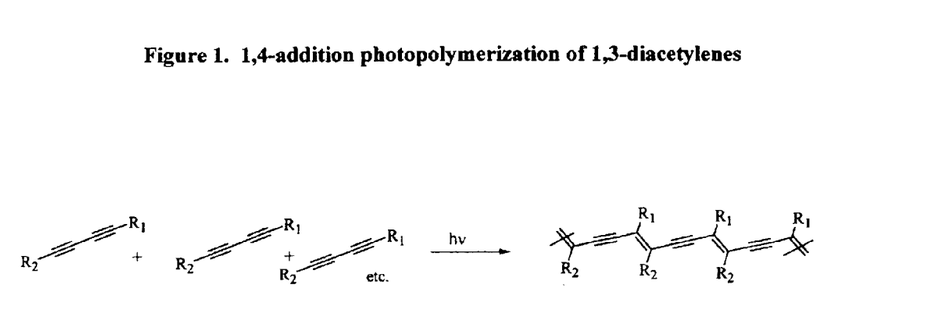
FIG. 1 illustrates the formation of polydiacetylene from diacetylene monomers.
Figure 2:
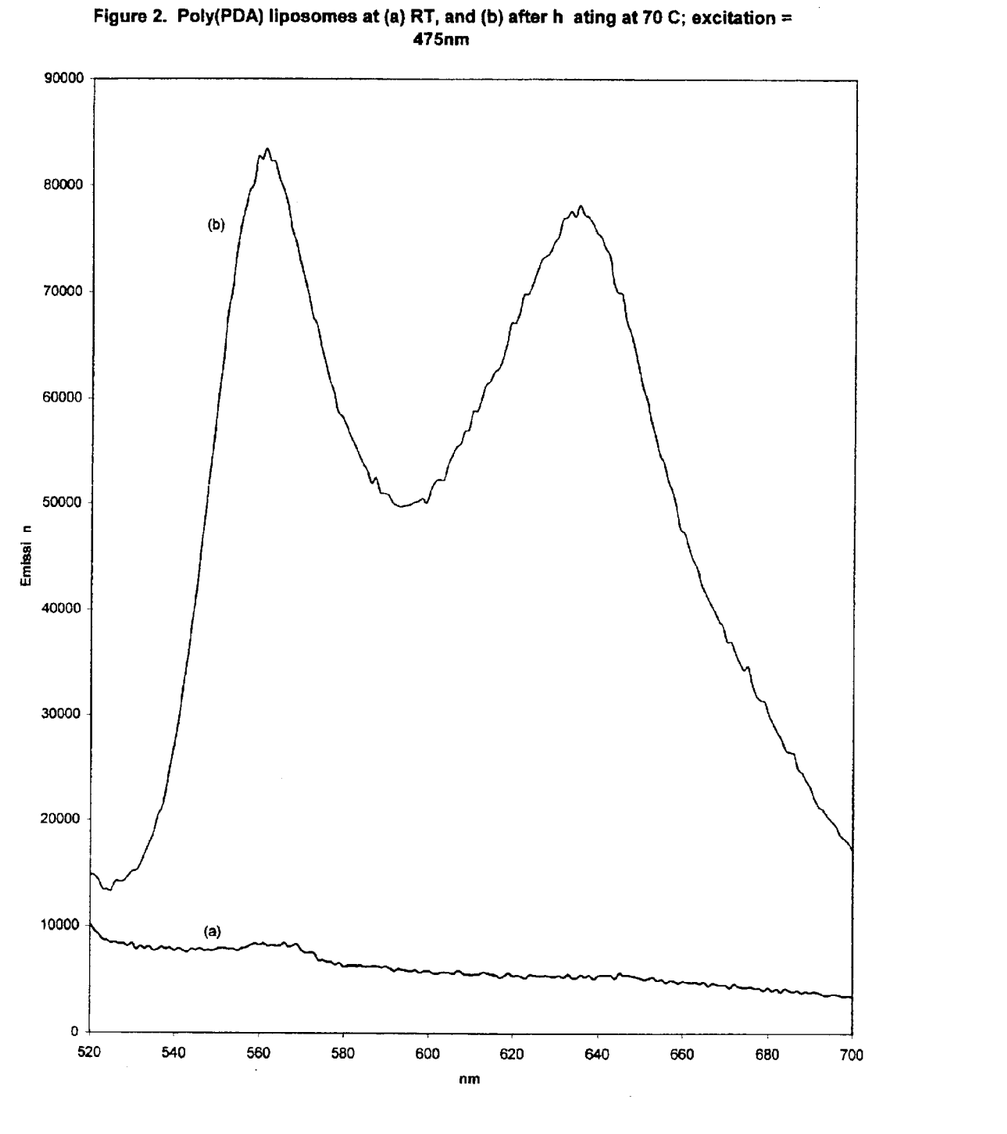
FIG. 2 illustrates the fluorescence spectrum of the non-fluorescent and fluorescent form of a polydiacetylene liposome employed in the process of the present invention.

Polydiacetylenes are conjugated polymers with backbones of alternating double and triple bonds formed from the 1,4-addition polymerization of 1,3-diacetylenes (FIG. 1). Polydiacetylenes generally absorb well in the visible region of the spectrum, and hence are highly colored, ranging from blue to yellow. There has been intense interest in the non-linear optic properties of polydiacetylenes and extensive study has been made of both the solvo-chromic properties of solubilized polydiacetylenes and the thermochromic properties of polydiacetylene films and single crystals. It is well known that to form polydiacetylene, the diacetylene monomers must be in an ordered packing to allow the polymerization to occur. It seems to be generally accepted, though the inventors are not bound herein, that disruption of the packing of the side chains can affect the conjugation length of the backbone, and hence the chromic properties.

Diacetylene monomers have been used to form various ordered systems, including crystals, liquid crystals, liposomes and films that were then polymerized to form the polymer. Liposomes have been made from monomers with two diacetylene chains and polar head groups (such as phosphotidylcholines, and its analogues) and from monomers with single diacetylene chains. The liposomes can be polymerized with UV light or γ-radiation. Monomer films have been formed by Langmuir Blodgett methods or cast from solvents and then also polymerized with UV light or γ-radiation. The choice of monomer structure, conditions of liposome or film formation, and polymerization conditions all affect the conjugation length of the polydiacetylene backbone, and hence the color of the system. Upon heating, these polymerized systems can undergo a change in the effective conjugation length, from the longer length forms (blue and purple) to the shorter length forms (red and yellow). This change has been attributed to the side-chains moving and repacking upon being heated. Soluble polydiacetylenes show solvo-chromic behavior and polydiacetylene films often change color upon exposure to solvent vapors. Polydiacetylene films and liposomes formed from diacetylene surfactants also often change color with change in pH. In the case of the packed polymer arrays that form the films and liposomes, it is generally accepted that changes in the environment that affect the organization and packing of the side chains coming off the conjugated backbone can affect the conjugation length and hence the chromic and electronic properties of the polymer.

These polydiacetylene films and liposomes have been suggested for chromogenic assays that depend upon color change (Charych et al, U.S. Pat. No. 6,001,556; Charych et al, U.S. Pat. No. 6,180,135; Charych et al, U.S. Pat. No. 6,080,423; Charych, U.S. Pat. No. 6,183,772; Charych et al, U.S. Pat. No. 6,022,748). It has been hypothesized by Clarych (Okada S. et al, *Acc. Chem. Res.*, 1998, 31, 229–239) that binding to a ligand incorporated in a blue polydiacetylene films or liposomes perturbs the side chains of the polydiacetylene and hence the conjugation length of the polydiacetylene and changes the color of the film or liposomes to red. The color change is proposed to be measured either by eye or by a UV/VIS spectrophotometer and comparison of the absorbance at a wavelength above 600 nm and the absorbance of a wavelength below 600 nm.

The phenomenon of fluorescence is distinct from the absorbance properties that give systems their color. In order to be fluorescent, the system must absorb one wavelength of light and then emit another. Upon absorbing the light, the system is excited to a higher energy state. It can then return to the ground state by a variety of mechanisms, most of which do not lead to fluorescence. These alternative, non-radiative, mechanisms for returning to the ground state lead to many strongly absorbing species to be non-fluorescent, and makes the prediction of which species will be fluorescent a difficult task and therefore not apparent to those skilled in the art.

For instance, while some organic systems with extended conjugation exhibit fluorescence, many more do not.

Along these lines, generally species absorb light in the ultraviolet and visible ranges. The ultraviolet wavelength range is approximately 190 nm–380 nm; the visible light range runs from approximately 380 nm to 800 nm. Upon absorption of the light the species move to a higher energy electronic excited state. What happens then determines if the species is fluorescent. If a species absorbs light at one wavelength, is excited to a higher energy state, and then emits light at a different wavelength and returns to the ground state, it is fluorescent (or phosphorescent). For fluorescence to occur the excited species must be capable of emitting light; generally for the fluorescence to be measurable the emitted light must be at a different wavelength than the excitation. The Stokes shift is the difference between the excitation and emission wavelengths. Most species that absorb light are not capable of light emission; they return to the ground state by a variety of non-radiative mechanisms. Furthermore, fluorescent species often absorb wavelengths of light that do not cause fluorescence, as well as absorbing wavelengths that do cause fluorescence. In short, absorbance of light is necessary for fluorescence but does not guarantee it.

On the other hand, color is an absorbance property; the colors we see are related to the wavelengths of light that the species is absorbing. For example if the species absorbs light primarily at 650 nm, we will see it as blue, while if it absorbs primarily at 550 nm, we will see it as red. Color arises from absorbance of light in the visible range. Most colored species are not fluorescent. If a colored species is fluorescent, it will normally appear one color, but when it is excited with the appropriate wavelength, it will glow with the color of the emitted light. For example, a fluorophore may look like an orange powder, but glow green under a UV lamp.

Polydiacetylenes can show fluorescence. However, their ability to fluoresce is dependent on the structural form and organization of the polymers (particularly the conjugation length and aggregation state), whether in solution, a film, or formed into liposomes or other three-dimensional structures.

It is known that polydiacetylene films have an intrinsic fluorescence when produced in the red or yellow form, and are not fluorescent (by conventional measurements) when the film is made in the blue form (Yasuda A. et al, *Chem. Phys. Lett.*, 1993, 209(3), 281–286). This fluorescent property of the films has been used for microscopic imagining of film domains and defects.

Ribi et al have suggested two sensors using polydiacetylene film fluorescence. The first sensor (Saul et al, U.S. Pat. No. 5,415,999 and U.S. Pat. No. 5,618,735) uses a red, fluorescent, polydiacetylene film layered with a fluorescence modulation reagent non-covalently associated with the film that modulates the measured emission of the film, e.g. by absorbing the emitted light, in the presence of an analyte. The fluorescent state of the film does not change during the assay; rather the emission is obscured or revealed by the action of the fluorescence modulation agent. The second suggested sensor (Ribi, U.S. Pat. No. 5,622,872) uses a film of specific composition for detection of an analyte by change in the fluorescence of a film of this composition. The films in the detection method claims comprise a polymerized film, polymerized from diacetylene monomers of the defined formulation $(A)_a(D)_aC_x(C\ C)_2C_yLB$ wherein A is a functional group used to link the film to an underlying substrate, a is 0 or 1, C is carbon, x and y are 1 or greater and (x+y) is in the range of 4–32, D and L are bond or linking groups and B is a specific binding member which binds to a specific analyte, one terminus of each monomer is proximal to the underlying substrate and the other terminus comprising B (i.e. the film is a mono-layer with every polydiacetylene side-chain either terminating in proximity to the underlying substrate, or in a binding member). Neither Ribi nor others, to our knowledge, have suggested detection of analytes using three-dimensional arrays of polydiacetylenes (e.g. liposomes or tubules) and measuring the change in fluorescence arising from the interaction of the analyte and the polydiacetylene three-dimensional array.

SUMMARY OF INVENTION

The present invention provides a sensing method that measures fluorescent changes in polydiacetylene films as they convert from the non-fluorescent form (generally blue or purple) to the fluorescent forms (generally red to yellow). More particularly, the present invention provides for the detection of an analyte in a sample, which comprises contacting the sample to be tested with a two-dimensional or three-dimensional array of a polydiacetylene backbone with substrate (e.g. a ligand or reactive substrate) covalently or non-covalently incorporated. The two-dimensional arrays of the present invention, i.e. films, comprise polymerized diacetylene two-dimensional arrays wherein no more that 90% of the diacetylenes terminate in groups that will bind specifically to the analyte (i.e. specific binding members). The ligand or reactive substrate has direct affinity for the analyte or can function as a binder to the analyte or can undergo a chemical or biological reaction or process with the analyte. The change in fluorescence is measured or detected to indicate the presence of the analyte.

The two-dimensional and three-dimensional polydiacetylene arrays of the present invention either change their fluorescent state upon interaction with the analyte, or change their fluorescence polarization upon interaction with the analyte. The change from the non-fluorescent form to the fluorescent forms of the polydiacerylene of the array, occurs due to interaction of the analyte of interest with the substrate incorporated in the array. Measuring the increase in the fluorescence of the array as the array changes from non-fluorescent to fluorescent can monitor these interactions as a new detection method, which is more sensitive than monitoring color change. This increase in sensitivity is necessary for the detection system to have actual utility as a sensor for many applications. It is also possible to begin with the array partially in the fluorescent form and measure the increase in fluorescence as the interaction with the analyte takes place. The arrays may also contain auxiliary fluorescence species (fluorophores), and the fluorescence of these fluorophores may be modulated by the polydiacetylene array and thus change as the polydiacetylene changes its fluorescent form.

The assay method of the present invention makes possible a continuous monitoring of the binding of the analyte. The analyte is added to the array and the fluorescence can be measured over time. Since no wash steps are required, the method of the present invention is relatively simple and inexpensive to carry out.

BEST AND VARIOUS MODES FOR CARRYING OUT INVENTION

In order to facilitate an understanding of the present invention the following definitions which are used herein are presented Substrate: A chemical or biological entity Reactive substrate: a substrate that can undergo a chemical or biological reaction or process Ligand: An entity or substrate that can preferentially interact with an analyte by a covalent or non-covalent binding interaction Analyte: Any entity (physical, chemical or biological) that is to be detected Non-fluorescent form: Low over-all fluorescence above 500 nm of the polydiacetylene as compared to its corresponding fluorescent form.

The two-dimensional and three-dimensional arrays employed according to the present invention comprise a polydiacetylene backbone. Incorporated in the polydiacetylene array is a ligand or reactive substrate that has direct affinity for the analyte or which can function as a competitive binder to the analyte or can react with the analyte. The ligand or reactive substrate is lipophilic or contains lipophilic portions or is conjugated to a non-polar or polar species rendering the overall conjugate lipophilic. The lipophilic or non-polar portions may contain diacetylenes or other polymerizable groups but it is not necessary. The arrays are prepared by polymerization of precursor diacetylene arrays. The diacetylene precursor two and three-dimensional arrays may also contain non-substrate species that are not diacetylenes. The two-dimensional arrays are formed from polymerization of two-dimensional arrays of diacetylenes wherein the arrays are comprised of not more than 90% of diacetylenes that terminate in functional groups that are specific binding groups for the analyte (i.e. that are members of specific binding pair with the analyte). More typically the two-dimensional precursor diacetylene arrays are comprised of 60% or less of diacetylenes that terminate in specific binding groups for the analytes.

The polydiacetylene backbones employed according to the present invention are known and need not be described herein in any detail and can range from being oligomeric (from the reaction of three or more monomers) to polymeric. For example see U.S. Pat. No. 6,001,556 to Charych et al, disclosures of which are incorporated herein by reference. The selection of a desirable polydiacetylene for a particular application can be determined by persons skilled in the art and aware of the disclosure in this application without undue experimentation.

In one embodiment of the invention the ligand or reactive substrate is bound to the polydiacetylene backbone, preferably via a linear structural linker. The linear structure linkers typically have two terminal ends, wherein the linkers are attached to their first terminal ends to the ligand or reactive substrate moieties, a portion of the middle of the linker is incorporated in the polydiacetylene backbone, and the remainder including the second terminal end becomes a side chain of the polydiacetylene. It is also possible for the second terminal end to be incorporated in the polydiacetylene backbone. In this embodiment the polydiacetylene is formed from polymerizing a three-dimensional or two-dimensional array of diacetylenes comprising a mixture of diacetylenes and of diacetylenes with the ligand or reactive substrate moieties attached covalently to the polymerizable diacetylene group. The array may also contain non-diacetylene species.

In another embodiment of the present invention the ligand or reactive substrates are incorporated in the polydiacetylene array without a covalent attachment between the polydiactylene backbone and the ligand or reactive substrate. The array may also contain other non-diacetylene species.

Also, side chains with ordering head groups are typically bound to the polydiacetylene backbone. The head groups are typically polar.

The polydiacetylene backbone is preferably in its non-fluorescent form.

The arrays are formed by polymerizing arrays of diacetylene monomers. The typical monomers are single or multi-tailed diacetylene surfactants with polar head groups. More typically used are single or bis-tailed diacetylene surfactants with polar head groups. The invention is not dependent on use of any specific diacetylene surfactant, tail structure, or polar head group, but can be used with any diacetylene monomer that can be polymerized to give polydiacetylene in its non-fluorescent form or polydiacetylene in a fluorescent form that is converted to a fluorescent form having a different emission and preferably a higher emission upon interaction with the analyte.

Materials typically used as head groups in the present invention include, but are not limited to: carboxylic acids, carboxylate salts, amides, ethanol amide, amines, ammoniums, imines, imides, alcohols, carbamates, carbonates, thio-carbamates, hydrazides, hydrazones, phosphates, phosphonates, phosphoniums, thiols, sulfates, sulfonates, sulfonic acids, sulfonic amines, sulfonamides, amino acids, peptides, nitro-functionalized moieties, carbohydrates, choline, ethylene glycol, oligiomeric ethylene glycol, poly(ethylene glycol), propylene glycol, oligiomeric propylene glycol, and poly(propylene glycol), and combinations thereof.

The ligands and reactive substrates employed in the present invention can be of a wide variety of materials and are defined herein as species incorporated in the polydiacetylene arrays that interact with analytes. The main criterion is that the ligand or reactive substrate has an affinity for the analyte of choice. The ligand or reactive substrate may be of a broad range, such as when a class of materials is to be assayed. Appropriate ligands include, but are not limited to: peptides, proteins, antibodies, antibody fragments, antigens and the epitopes thereof, enzymes, carbohydrates, nucleic acids, amino acids, crown ethers, cage compounds, small molecules, organo-metallic compounds, salts, or any biologicai or organic compound or species which bind to analytes. Appropriate reactive substrates include phospholipids, peptides, proteins, protease substrates, kinase substrates, carbohydrates, nucleic acids, amino acids, or any biological, organic or organo-metallic compound or species that can undergo a chemical or biological reaction or process. Analytes include, but are not limited to: membranes, receptors, cells, bacteria, viruses, toxins, proteins, enzymes, proteases, kinases, antigens, antibodies, nucleic acids, small molecules, and any biological, organic or organo-metallic species that can interact with a ligand or reactive substrate.

Some specific ligands include $G_M1$-ganglioside, sialic acid, serotonin, diactadecyl glycerylether-$\beta$-gluocoside, anti-Salnonella antibodies, anti-Listeria antibodies, anti-Campylobacter antibodies, anti-Chlamydia antibodies, anti-Cryptosporidium antibodies, anti Escherica coli antibodies, HIV protease substrate, MAP kinase substrates, MEK kinase substrates, and hexokinase. Some specific reactive substrates include dimyristoyl phosphotidylcholine, dipalmitolyl phosphotidylcholine, peptides containing myelin basic protein residue sequences, peptides containing tyrosine hydroxylase residue sequences, peptides containing MAP kinase residue sequences, and phosphatidylinositol-4,5-biphosphonate substrate for Phosphoinositide 3-kinase. Some specific analytes include influenza virus, cholera toxin, phospholipases such as phospholipase $A_2$, HIV protease, MAP kinases, MEK kinases, Phosphoinositide 3-kinases, Salmonella, Listeria, Eschericia coli, Chlamydia, Cryptosporidium, and Campylobacter.

When the arrays of the present invention are to be secured or anchored to a support surface, the tails of the lipids can be selected to provide this function.

The two-dimensional and three-dimensional arrays of the present invention can be produced in any number of forms. One of the suitable three-dimensional array forms that can be produced are liposomes. The liposomes can be formed in a number of different sizes and types. For instance, it is possible to form the liposomes as simple bi-layer structures. Additionally, they can be multi-layered in an onion type structure. Their size can also be varied. A suitable two-dimensional array form that can be produced is a film. The film can be mono-layered, bi-layered, or multi-layered.

Numerous other shapes can also be produced. Lamellae (Rhodes et al, Langmuir, 1994, 10, 267–275), hollow tubules and braids (Frankel et al, J. Am. Chem. Soc., 1994, 116, 10057–10069.), crystals, lyotropic and thermotropic liquid crystalline phases, gels and amorphous structures are among the other shapes that can be formed. When these assemblies are immobilized they can collectively form even larger constructs.

Diacetylene liposomes can be converted to tubules before polymerization by controlled cooling, concentration changes, or addition of ethanol. The tubules can be photopolymerized to give the non-fluorescing form of polydiacetylene, and then used in assays with fluorescence monitoring. Polydiacetylene can also be formed as blue or red gels with a net-work structure of aggregated fibers. Polydiacetylenes have been used in the formation of composite materials, including layering with inorganic clays.

Two or three-dimensional arrays of diacetylene long chain monomers are prepared with ligands or substrates incorporated for use in chemical reactions. These ligands or substrates can be functionalized diacetylenes, or simply be sufficiently lipophilic to mix with the diacetylene monomers. The arrays are usually in the form of mono-layer or multi-layer films, or liposomes in solution. Film arrays of diacetylenes or polydiacetylenes may be used in the free form, or supported on glass, ceramic, polymer, paper, metal, or other surfaces. The supports may be porous, including, but not limited to, nano and micro porous membranes. Diacetylene coatings may also be cast onto glass, ceramic polymer, paper,metal or other surfaces and photopolymerized to give the polydiacetylene array described above.

Diacetylene and polydiacetylene liposomes may be attached to, supported on, or absorbed in, solids, including, but not limited to: polymers such as polystyrene, polycarbonate, polyethylene, polypropylene and polyfluorocarbons such as Teflon®; silicon chips; beads; filters and membranes; glass; gold; silica; sephadex; sepharose; porous or swelling solids such as polyacrylates and polyacetonitrile; and sol-gels. In the icase of diacetylene liposomes and film arrays, they are polymerized after incorporation with or attachment to the solid support.

A preferred embodiment of solid supported polydiacetylenes is as an array on nano-porous membranes. A more preferred embodiment is as an array on polycarbonate nano-porous membranes.

We have discovered that diacetylene liposomes can be forced in and onto membranes including 100, 200 and 400 nm membranes and photopolymerized to create non-fluorescent polydiacetylene. These membranes are stable at room temperature, in air, and exposed to light, for at least 12 months. The polydiacetylene array exhibits some resistance to abrasion. It seems possible, though the inventors are not bound thereby, that the diacetylene liposomes partially pass through larger pores at the membrane surface before being trapped by smaller pores within. The polydiacetylene arrays can be converted from the non-fluorescent to the fluorescent form when exposed to appropriate reagents.

Nanoporous membranes are available in many materials, including: alumina, polyfluorocarbons such as Teflon®, nylon, polycarbonate, glass and polyvinylene difluoride (PVDF), and also in a variety of pore sizes. We envision using any of these membrane types with pore sizes up to about 600 nm for preparing solid supported polydiacetylenes. The polydiacetylene-coated membranes can then be incorporated into filter and flow cells, used as swabs or test strips, or adhered to any solid support.

One embodiment of the invention uses a filter or flow cell containing a non-fluorescent form polydiacetylene array with a substrate incorporated, in/on a membrane. A solution of an analyte is passed through the filter or flow cell and then the fluorescence of the membrane is read. The array may contain fluorophores that does not interact optically or electronically with the polydiacetylene. The fluorescence emission of these fluorophores may be monitored separately as an internal calibration standard. The array may also contain fluorophores that do interact optically or electronically or through resonance coupling with the polydiacetylene.

The diacetylene 2-dimensional and 3-dimensional structures are photopolymerized with UV light, or γ-radiation, to give organized polydiacetylenes with the longer conjugation lengths characterized by absorption maximum in the range of 500–800 nm, preferably in the range 600–750 nm, and a blue to purple color. The photopolymerization results in creating mainly the non-fluorescing form and therefore exhibiting low overall fluorescence relative to the background. The term "non-fluorescent form" as used herein also refers to these polymers which have low overall fluorescence exhibiting a fluorescent signal above 500 nm that is only about 1–3 times that of the background and less than that of the corresponding fluorescent form. Typically the "non-fluorescent form" exhibits a fluorescent emission above 500 nm that is at least in about 10% lower and more typically at least about 50% lower than that of the corresponding fluorescent form. Some diacetylene 2-dimensional and 3-dimensional arrays give polydiacetylene in the fluorescent forms upon photopolymerization; these may still be used in assays if interaction with the analyte converts the arrays to a fluorescing form having a different measurable emission and preferably from a lower-fluorescing form to a higher-fluorescing form.

The fluorescence of the polymerized arrays is measured, they are exposed to the analyte of interest for a sufficient length of time so that either binding or chemical/biological reaction can occur, and then the fluorescence is measured again. The binding, or chemical/biological reaction, causes a conversion of the array from the non-fluorescing form to a fluorescing form, characterized by absorption maxima below 590 nm, and a red, orange, green or yellow color. The polydiacetylene fluorescence of the fluorescent form may be excited by light with wavelengths between 300 and 600 nm, and consists of a broad fluorescence above 500 nm with one or two maxima though the invention is not bound by these specifics. A rise in the polydiacetylene fluorescence after, or during, exposure to the analytes or species of interest, indicates binding or reaction. The fluorescence can also be measured periodically during the exposure to follow the course of the interaction and elucidate the kinetics.

This sensing method can also be used to measure the inhibition of binding to the ligands, or reaction with the substrate, by active compounds. In the case of inhibition measurements the inhibitor, or test compound, is added to the polydiacetylene arrays. The active species, which can either bind to a ligand or react with a reactive substrate, is also added. If the samples show increase in fluorescence similar to the increase in fluorescence shown by control samples without the test compound added this indicates that the potential inhibitor is not suppressing the activity of the active species. If the samples maintain a low level of fluorescence, relative to the control samples, or the fluorescence increases only a fraction of the rise seen in the control samples, this indicates inhibition of the activity of the active species by the test material.

Figure 3:
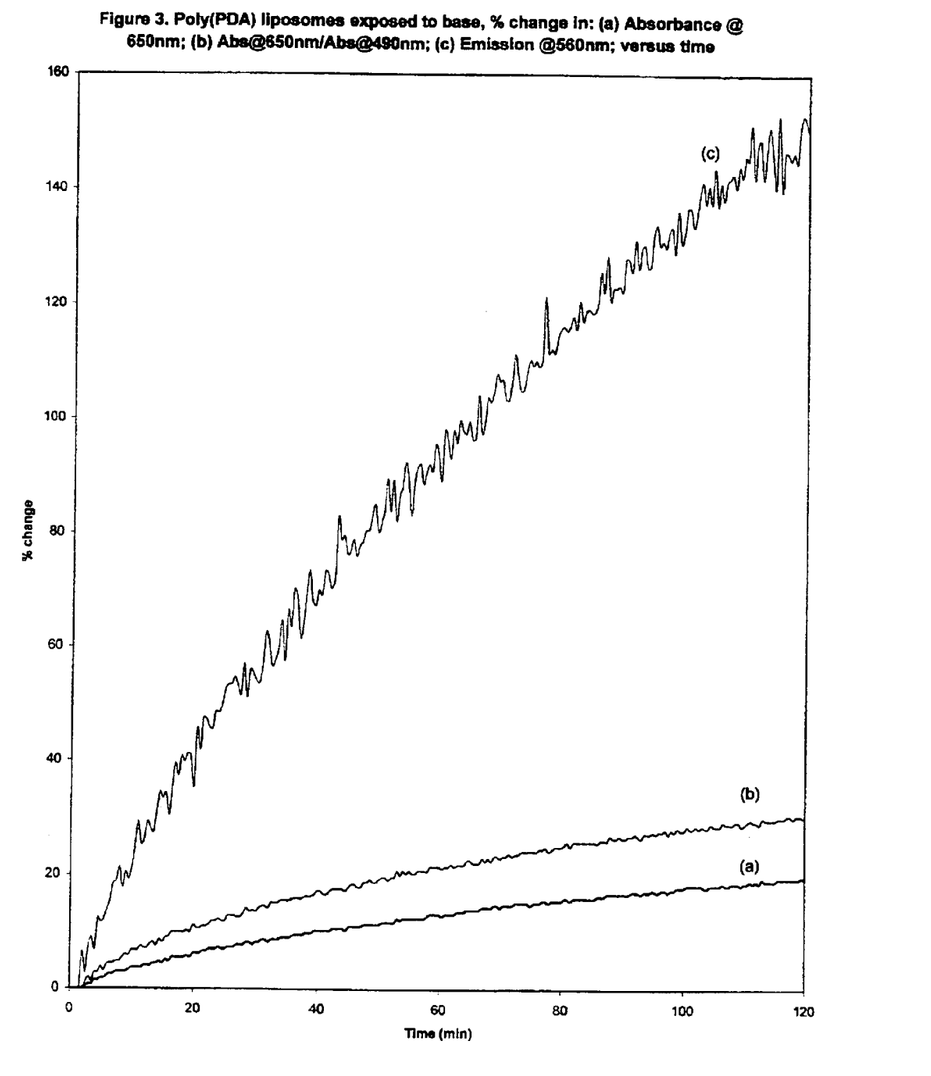
FIG. 3 illustrates the changes in absorbance and fluorescence of polydiacetylene liposomes as they convert from one form to the other.

The conditions that cause conversion to the fluorescent form also may cause chromic changes that appear to the eye as a blue to red shift, and can be quantified by measuring the UV/VIS absorption spectrum. Change in fluorescence and change in absorbance at specific wavelengths do not necessarily linearly correlate (FIG. 3). It seems likely, though the inventors are not bound herein, that rise in the fluorescence emission can be a result of either a rise in the population of shorter conjugation length polydiacetylene backbones, or a decrease in the quenching longer conjugation length polydiacetylene backbones, or both. The relative change in fluorescence can be an order of magnitude, or more, greater than the relative changes measured in the UV/VIS absorption spectrum upon this transformation. This means that fluorescence can provide a more sensitive measure of change in the liposomes than the direct chromic response. This increase in sensitivity makes the novel fluorescence detection method of use in many areas where colorimetric detection would simply not be sufficient. These include drug discovery assays and pathogen detection. For films, the fluorescent/non-fluorescent properties of the polydiacetylenes can be used as a new chemical sensing method and would also provide increased sensitivity compared to calorimetric detection in immobilized sensing systems. Fluorescence detection also allows sensing platforms to use opaque supports, whereas calorimetric detection requires clear (e.g. quartz glass or UV/VIS-transparent plastic) supports.

The fluorescence can be read with any equipment known in the art for fluorescent measurements, including, but not limited to, fluorometers with cuvette and fiber optic attachments, plate readers, hand held readers, fluorescence microscopes, CDC cameras, and by eye; This sensing method may be readily used in the multi-well plate formats of high-throughput screening.

This new sensing method can be used with appropriate ligands incorporated in the polydiacetylene arrays to detect a wide variety of chemical and biological species in air and solution, including, but not limited to: small organics (molecular weight <1000 g/mole), solvents, toxins, peptides, proteins, viruses, bacteria, chemical and biological warfare agents, and the like. The method can be used with appropriate substrates incorporated in the polydiacetylene arrays to detect a wide variety of Ha, chemically and biologically reactive species in air and solution, including, but not limited to: bases, acids, Lewis acids, Lewis bases, nucleophiles, electrophiles, oxidizers, reducers, and enzymes. This method can also be used to measure inhibition of binding or reactivity. The method of the present invention can be used in fields including, but not limited to: drug-discovery, medical diagnostics, food safety, pathogen detection, environmental monitoring (including monitoring of the production, storage and use of chemical and biological warfare agents), and basic research.

It is believed that increasing the separation of the conjugated polymer chains can enhance the fluorescence of the fluorescent form of the polydiacetylene further. Separation of the polymer chains has been suggested as enhancing the fluorescence by decreasing the amount of self-quenching. It has been shown in the crystal form of polydiacetylene that fluorescence can be achieved only by separating the polymer chains (Lecuiller R. et al., *Phys. Rev. Lett.*, 1998, 80(18), 4068–4071). It is possible to dilute the polymer array with other non-diacetylene surfactant species while still maintaining the liposome or film structure. Alternatively the side chains can be functionalized with bulky groups to force the polymer backbones apart a given distance, or the polydiacetylene can be prepared as a co-polymer with either a conjugated or non-conjugated polymer. Another approach is to reduce the extent of polymerization, so the polydiacetylene segments are isolated in an array of diacetylene monomers.

In a further embodiment of the invention the polydiacetylene arrays may incorporate other fluorescent species. These fluorophores may be organic, biological, inorganic or polymer compounds, complexes or particles. The fluorophores can enhance the magnitude of the change in the fluorescence of the polydiacetylene arrays as they change from the non-fluorescing to the fluorescing form. The fluorescence of these fluorophores can also be monitored during this conversion, either as an internal standard if the fluorophore's fluorescence is not affected by changes in the polydiacetylene, or as an additional measure of the conversion when the fluorophore's fluorescence does change. In addition certain fluorophores can undergo excited state energy transfer processes that change the overall fluorescence of the array, and increase the quantum yield.

Many of the fluorophores are lipophilic and are expected to incorporate into the alkyl region of the liposome, while others are polar or charged and are expected to end up in the head group region/aqueous interface, or in the water solution. The change in both the liposomes' fluorescence and the added fluorophore's fluorescence have been monitored as the liposomes changed from the non-fluorescing to the fluorescing form under the action of heat, chemical reactions, or during analyte detection. Various fluorophore additives had the effect of enhancing the percentage change in the liposome fluorescence response upon changing from the non-fluorescing form to the fluorescing form. The fluorescence of the added fluorophore was also monitored and also indicated the change in the liposome form with some fluorophores showing an increase in their fluorescence and others a decrease.

The added fluorophores may optically and/or electronically interact with the polydiacetylene polymer. There are several ways that the fluorophores and the array can optically/electronically interact, including but not limited to the following means:

(1) By the fluorophore absorbing the fluorescence of the array or by the array absorbing the fluorescence of the fluorophore.

(2) By the fluorophore absorbing the excitation light, becoming excited and then transferring energy from its excited state to the polydiacetylene array causing it to fluoresce. This process is known as Resonance Energy Transfer (RET) and also as Fluorescence Resonance Energy Transfer (FRET). This RET process allows the polydiacetylene fluorescence to have the time decay properties of the fluorophore.

(3) By the polydiacetylene array, in its fluorescent form, absorbing the excitation light and then transferring the energy from its excited state to the fluorophore leading to the fluorophore fluorescing. This RET process can lead to an increase in the effective Stokes shift of the system and also increase the overall quantum yield.

(4) By the excited state of the fluorophore transferring an electron to the array or by the excited state of the array transferring an electron to the fluorophore. This process is known as Photoinduced Electron Transfer (5) By the array absorbing the excitation light needed for fluorophore fluorescence or the fluorophore absorbing the excitation light needed for array fluorescence.

(6) By the fluorophore quenching the fluorescence of the array.

(7) By the array quenching the fluorescence of the fluorophore.

Addition of fluorophores to the polydiacetylene array can make it possible to increase the extent of the change in fluorescence of the array during an assay, thus increasing assay sensitivity; and also to monitor the fluorescence of the fluorophore during the assay as a second measure of change in the polydiacetylene array caused by the analyte. The RET interaction between the fluorophore and the polydiacetylene array is discussed below.

Fluorescence Resonance Energy Transfer (RET)

While fluorescence monitoring using the intrinsic fluorescence of polydiacetylene is an improvement over absorbance (i.e. colorimetric) monitoring, polydiacetylene is a relatively weak fluorophore. Fluorescent polymers are often poor fluorophores because the conjugated chains can act as excited state traps and provide mechanisms for non-radiative relaxation of the excited state, leading to quenching of the fluorescence (Warta R. et al, *J. Chem. Phys.*, 1988, 1, 95–99). It is theorized that the long conjugation lengths of blue polydiacetylene provide very effective trapping of the excited states which is why the blue form is effectively non-fluorescent (Morgan J. et al, *Chem. Phys. Lett.*, 1992, 196, 455–461). Red and yellow polydiacetylene arrays actually contain mixtures of polymer chains of different conjugation lengths, and so it is quite likely that inter-chain quenching as well as intra-chain quenching, reduces the fluorescence of the shorter conjugation lengths.

The overall fluorescence of the polydiacetylene arrays can be increased by incorporating certain fluorophores in the lipid regions, at the lipid/water interface and in the water solution itself The inventors hypothesize, although they are not bound thereby, that certain fluorophores accept energy from the excited fluorescent PDA chains via resonance energy transfer ("RET" a.k.a. "FRET") and then fluoresce. The RET process appears to short-circuit the inner-chain quenching mechanisms and leads to a 20–30 fold increase in the fluorescence intensity of the system. The RET process with certain fluorophores also significantly increases the Stokes shift from <100 nm to >200 nm. This is important when using plate readers to measure fluorescence as they often have less than optimal optics, or when reading the fluorescence of solids where there is usually high background from reflection of the excitation light off the surface. The incorporated fluorophores are directly excited by the wavelengths used to excite the polydiacetylene only to a minor extent and so they do not make the non-fluorescent polydiacetylene arrays containing these fluorophores significantly fluorescent.

It is also possible for the fluorophores to transfer energy from their excited states to the fluorescent form of the polydiacetylene array, causing it to fluoresce. A fluorophore can be excited at a wavelength that polydiacetylene is not excited by, and then transfer energy to the polydiacetylene leading to polydiacetylene fluorescence. This also may increase the effective Stokes shift of the overall polydiacetylene array. If the fluorophore has a long lifetime, for example certain terbium and europium compounds have long excited state decay times, the polydiacetylene fluorescence decay will have a similar lifetime. This makes it possible to perform time-resolved fluorescence (TRF) measurements using polydiacetylene arrays and common TRF readers (e.g. the Victor$^2$V).

An additional assay method measures changes in polarization of fluorescent polydiacetylene liposomes to detect binding or reaction of analytes of interest with the liposomes. For this method the change in the polarization of the liposome fluorescence is measured rather than the change in the intensity of the fluorescence.

Fluorescence Polarization for Detection

The fluorescence polarization detection method depends on the change in rotation (or tumbling) of fluorescent polydiacetylene liposomes or other fluorescent three-dimensional arrays when the analytes of interest bind to, or react with, the arrays.

The three-dimensional fluorescent polydiacetylene arrays are excited with polarized light. If the arrays emit light before rotating the emission will also be polarized. A polarizer is placed in the emission path and will filter out all emitted light (ie fluorescence) that does not have the appropriate polarity. If the arrays have time to rotate significantly after their excitation and before emission, the emission will be depolarized. After an analyte binds to the arrays, there should be a significant reduction in the tumbling rate if the analytes is approximately the same size or larger than the arrays. This will lead to the emission being more polarized. It is also possible that the analyte will bind to multiple arrays; this would retard rotation further and increase the polarization. If the arrays bind to multiple analytes the polarization also would be increased. If the analyte degrades or alters the structure of the liposome or other three-dimensional polydiacetylene array, or de-aggregates clusters of liposomes or other three-dimensional polydiacetylene arrays, through reaction with a reactive substrate incorporated in the array, this could change the tumbling rate of the array, and hence its fluorescence polarization. If the analyte de-aggregates clusters of liposomes or other three-dimensional polydiacetylene arrays, through reaction with or binding to substrates incorporated in the arrays, this could change the tumbling rate of the arrays, and hence the measured fluorescence polarization. If the analyte is bound to a surface, including the surface of a microbead (diameters typically in the nanometer and micron range, up to a millimeter) or the surface of a macrobead (diameters typically in the millimeter and greater range), or to a colloidal particle, and a three-dimensional polydiacetylene array binds to the analyte the fluorescence polarization of the array also may change.

A preferred embodiment of this detection method uses fluorescent polydiacetylene liposomes incorporating ligands and/or reactive substrates as the three-dimensional arrays.

The change in polarization is determined by measuring the intensity of emission through a polarizer that is parallel ($I_P$) and the emission through a polarizer that is perpendicular ($I_S$) to the excitation polarizer. The polarization is calculated: $P=(I_P-I_S)/(I_P+I_S)$; as binding occurs $I_P$ increases and $I_S$ decreases, and the polarization increases. A comparable method is to track the anisotropy, $r=(I_P-I_S)/(I_P+2I_S)$, instead of the polarization.

EXAMPLES

The following non-limiting examples are presented to further facilitate an understanding of the present invention.

In the following examples, unless otherwise stated, the diacetylene fatty acids were purchased from Farchan or GFS or synthesized in-house. Acetylene compounds were purchased from GFS or Lancaster. Reagents were obtained from Aldrich and Fisher Scientific. Dimyristoyl phosphatidylcholine (DMPC), 1,2-distearoyl-sn-glycero-3-phosphorylethanolaminocarproylmaleimide, bee venom phospholipase $A_2$ (PLA$_2$), monosialoganglioside $G_{M1}$, and cholera toxin B sub-unit were purchased from Sigma. Organic fluorophores were obtained from Molecular Probes and Aldrich; terbium and europium salts from Alfa Aesar. *Chlamydia trachomatis* antibodies (anti-MOMP) were obtained from ViroStat; *Chlamydia trachomatis* elementary bodies (EBs) were purchased from Advanced Biotechnologies. H$_2$O was purified by ultra-filtration through a Millipore Milli-Q Plus system. Solvents were obtained from Fisher Scientific in Optima grade unless otherwise specified; anhydrous solvents were obtained from Aldrich.

Probe sonication was achieved using an Imaging Products Sonic 300 V/T fitted with a micro-tip, with the power set to ~25%. Bath sonication was achieved using a Fisher Scientific FS140H sonicator, filled with water and heated to the appropriate temperature. Photopolymerization was achieved using a UV-oven capable of delivering calibrated energy doses of UV light around 254 nm. Fluorescent spectra were measured in cuvettes and in 96-well plates (black and white untreated polystyrene) with a SPEX Fluoromax-2 with a MicroMax plate reader attachment, UV/VIS spectra were measured in 96-well plates with a Molecular Devices Spectramax-250 plate reader. Assay data were collected using both the SPEX Fluoromax-2 plate reader, and Wallach Victor$^2$ and Victor$^2$V readers. $^1$H and $^{13}$C spectra were obtained by Acorn NMR, Livermore Calif.

Diacetylene fatty acids that were not commercially available were synthesized according to literature methods by the copper (I) mediated coupling of the appropriate 1-iodo-1-yne hydrocarbon and ω-yne carboxylic acid (Tieke B. et al, Angew. Chem Int. Ed. Eng., 1976, 15(12), 764–765). The 1-iodo-1-yne hydrocarbon was prepared by deprotonation of the corresponding 1-yne hydrocarbon with one equivalent of butyllithium in anhydrous hexane at room temperature under argon for one hour, followed by addition of 1.02 equivalents of iodine. The reaction was stirred at RT for 6 hours followed by 15 hours at −20° C. The reaction was quenched with 1M hydrochloric acid, and the product extracted into ethyl ether. The combined ether extracts were washed with saturated sodium thiosulfate solution five times, saturated sodium chloride two times, dried with magnesium sulfate and filtered. The solvent was removed under partial pressure to afford the crude 1-iodo-1-alkyne in 98% yield. The crude product was diluted with isopropyl alcohol and used in the next reaction within two hours or was stored in the undiluted form at −20° C. for no more than ~20 hours.

One equivalent of the ω-yne carboxylic acid was dissolved in 1 M potassium hydroxide solution containing 1.3 equivalents of KOH under argon. A catalytic amount (~0.1 equivalents) of hydroxy ammonium chloride was added to the solution. Cuprous chloride, 0.25 equivalents, was dissolved in 70%. ethylamine in water containing 4.4 equivalents of ethylamine. This solution was added to the deprotonated fatty acid solution and the mixture chilled in an ice/water bath. The crude 1-iodo-1-alkyne (1.05 equivalents) was added in isopropyl alcohol (approximately two volumes of iodo-alkyne solution to one volume of reaction mixture), the flask covered with foil to protect the contents from light and the reaction stirred at 0° C. for 1 hour. The reaction was then warmed to RT and stirred for another ~20 hours. The reaction was quenched with 1M sulfuric acid, and the product extracted into ethyl ether. The combined ether extracts were washed with each of: water, saturated sodium thiosuiphate and saturated sodium chloride repeatedly, and then dried over magnesium sulfate. The mixture was filtered and the solvent removed under partial pressure to give the crude product in quantitative yield. The diacetylene fatty acids were purified either by repeated recrystallization from chloroformnhexane and hexane, or by flash column chromatography on silica eluted with an increasing percentage of isopropanol in chloroform followed by recrystallization from hexane. Purity was determined by thin layer chromatography on silica (eluted with 5% methanol in chloroform), and $^1$H-NMR and $^{13}$C-NMR analysis.

Chloroform solutions of diacetylene surfactants were prepared by dissolving the appropriate amount of surfactant in chloroform to make a 2.0 mM solution and then filtering the solution through 0.22 micron pore PTFE filters to remove any polymer. Diacetylene liposome solutions were prepared according to general methods presented in the literature (Hupfer B. et al, Chem. Phys. Lipids, 1983, 33, 355–374; Spevak et al, J. Am. Chem. Soc., 1993, 115, 1146supplementary materials; Reichart A. et al. J. Am. Chem. Soc., 1995, 117, 829-supplementary materials) by drying organic solutions of the diacetylene surfactants together with any additives (e.g. ligands or reactive substrates, and/or fluorophores), adding water or buffer to bring the combined materials to approximately 1 mM overall, probe sonication to disperse the materials, filtration through a 0.8 μm pore size cellulose acetate filter and chilling at 4° C. or 10° C. overnight.

Chlamydia trachomatis antibodies (anti-MOMP) were cleaved into identical halves by reduction of the hinge disulfide bonds with 2-mercaptoethylamine hydrochloride (MEA) (Hermanson G., Bioconjugate Techniques, 1996, Academic Press, San Diego, p83). The antibody solution (0.950 mL, supplied as 4–5 mg/mL in 2 mM $KH_2PO_4$/8 mM $Na_2HPO_4$/155 mM NaCl, pH 7.2) was combined with 0.02 mL 2 mM $KH_2PO_4$, 0.08 mL 8 mM $Na_2HPO_4$ and 0.02 mL 500 mM EDTA, at pH 7.4. MEA (6 mg) was added and the reaction tube flushed with argon and incubated at 37° C. for 90 minutes. The reaction solution was removed and dialyzed for ~20 hours (10,000 MWCO dialysis cassette) against 0.1 M $Na_2$HPO4/0.15M NaCl buffer at pH 7.2 (3 changes of ~750 mL).

The free thiol groups were used to conjugate the antibody halves to 1,2-distearoyl-sn-glycero-3-phosphorylethanolaminocarproylmaleimide (PE-M) to provide the antibodies with lipid tails (Hermanson G., ibid, pp463–465). PE-M (0.21 mg) was added to the dialyzed cleaved antibody halves, the reaction tube flushed with argon and then bath-sonicated at 37° C. with occasional vortex mixing over 2 hours to disperse the PE-M. The tube was then incubated at 37° C. for one hour, and the solution subsequently dialyzed for ~20 hours (10,000 MWCO dialysis cassette) against 1.5 mM $KH_2PO_4$/1 mM $Na_2HPO_4$/137 mM NaCl/2.7 mM KCl at pH 7.1 (3 changes of ~750 mL).

Anti-chlamydia trachomatis antibody halves, conjugated to PE-M, were inserted into unpolymerized diacetylene liposomes via detergent dialysis using deoxycholate (Huang A. et al, J. Bio. Chem., 1980, 255(17), 8015–8018). Liposome solution (1.0 mL, 1 mM in lipid) was combined with 6–7 μL of the conjugated antibody halves solutions, 56 μL of deoxycholate solution (12.5% in water) and 100 μL of 15 mM $KH_2PO_4$/10 mM $Na_2HPO_4$/1.37M NaCl/27 mM KCl at pH 7.4. The mixture was then dialyzed at 4° C. for ~20 hours against 10 mM KCl/1.5 mM $KH_2PO_4$/1 mM $Na_2HPO_4$, at pH 7.1, using a 10,000 MWCO cassette and three changes of ~750 mL.

Example 1

Liposomes were formed from 10,12-pentacosadiynoic acid (PDA) in water and photopolymerized with 400 mJ/cm$^2$ of UV energy at around 254 nm. The solution was dilutedto 0.1 mM in original lipid and the fluorescence spectrum measured. The solution was heated at 63° C. for ten minutes, and the fluorescence spectrum measured again. The fluorescence of the two maxima increased 350% and 400%. This shows conversion from the non-fluorescent to the fluorescent form of the polydiacetylene liposomes with heating.

Example 2

Additional solutions of polymerized liposomes were prepared as for Example 1 with fluorophores added to the PDA at 5% molar concentration. The fluorescence spectra were taken, both of the polymerized liposome fluorescence and of the fluorophore fluorescence, the samples heated at 63° C.–65° C. for 10–15 minutes, and the spectra measured again. The data are presented in Table 1. The liposome fluorescence increased by up to 13-fold, and the fluorophore's fluorescence also varied from dropping 16% to increasing 20.3-fold (2,030%).

TABLE 1

Change in Fluorescence after 10–15 m at 63° C.–65° C.

| Added Fluorophore | A[1] | B[2] | C[3] |
|---|---|---|---|
| 16-(9-anthroyloxy) palmitic acid | 24% | 646% | 633% |
| BODIPY ™ TR-Cadaverine | 74% | 314% | 487% |
| Dapoxyl ™-AES | 11% | 378% | 310% |
| BODIPY ™ 493/503 | −16% | 76% | 274% |
| Eu(THD)$_3$* | — | 730% | 770% |
| Tb(THD)$_3$* | — | 1200% | 1300% |
| 1,1′-dioctadecyl-3,3,3′,3′-tetramethylindodicarbocyanine,4-chlorobenzenesulfonate salt (DIC-18(5)) | 2,030% | 540% | 598% |
| BODIPY ™ 630/650-X | 1,910% | 330% | 750% |
| none | — | 347% | 401% |

[1]A = change in fluorophore's fluorescence
[2]B = change in poly(PDA) liposome's fluorescence at 560 nm
[3]C = change in poly(PDA) liposome's fluorescence at 625 nm or 630 nm
*THD = tris(2,2,6,6,-tetramethyl-3,5-heptadionate)

Example 3

PDA liposomes were prepared in water and photopolymerized as for Example 1. Diluted solutions were prepared using equal volumes, with H$_2$O and with 25 mM sodium bicarbonate to approximately 0.1 mM in original lipid. The liposome fluorescence spectra of the water-diluted samples were measured, and after 30 minutes the spectra of the base diluted samples were also measured. The percentage change in the fluorescence of the 560 nm maximum varied from a 55% increase for the plain poly(PDA) liposomes to 565% increase for one of the liposomes with fluorophore samples (Table 2).

TABLE 2

Change in poly(PDA) Liposome Fluorescence with Base

| Fluorophore | % Change |
|---|---|
| None | 55% |
| 1-Pyrenebutanol | 274% |
| 16-(9-Anthroyloxy)palmitic acid | 131% |
| BODIPY ™ TR-Cadaverine | 253% |
| Dapoxyl ™-AES | 78% |
| BODIPY ™ 665/676 | 165% |
| BODIPY ™ 493/503 | 232% |
| 7-Amino-4-methylcoumarin | 565% |

Example 4

Liposomes were prepared from PDA in water and photopolymerized as for Example 2. The poly(PDA) liposome solution was diluted 1:1 with 25 mM sodium bicarbonate to approximately 0.1 mM in original lipid. A portion of the sample was placed in the quartz micro-cell (250 µL) of the Fluoromax2 and the fluorescence emission at 560 nm monitored over two hours. The absorbance of another portion at 650 nm, 560 nm, and 490 nm was simultaneously monitored over two hours. The percentage changes of the measurements from the initial values were calculated for each data point (% change=100×[(V(t)−V(0))/V(0)] where V(t) is the measured value at time point t, and V(0) is the initial value). The % change data for the fluorescence and absorbance of the poly(PDA) liposomes are shown in FIG. 3 demonstrating clearly that the change in the fluorescence signal was significantly greater than the change in the absorbance.

Example 5

1 µM and 5 µM solutions of poly(PDA) liposomes were prepared by appropriate dilution of a stock polymerized liposome solution (see Example 1) with 25 mMNaHCO$_3$ causing the conversion of the poly(PDA) liposomes to the fluorescent form. The UV/VIS absorbance of the samples (100 µL each) was measured using a Molecular Devices plate reader with a 96-well Costar TV/VIS plate. No absorbance was detected above a water background at 650 nm, 620 nm, 560 nm and 490 nm specifically, and over a scan of 350 nm to 750 nm generally, for either sample. The fluorescence spectra of the solutions were measured using the SPEX Fluoro-Max 2 and a quartz micro-cell and excitation at 490 nm. Fluorescence signals at 560 nm of approximately 4 times and 5 times the water background were measured for the 1 µM and 5 µM solutions respectively. When the fluorescence of the solutions in a black Griener 96 well plate (100 µM each) was measured with the VICTOR$^2$ plate reader with excitation of 485 n=, the 1 µM and the 5 µM liposome solutions both showed significant signal at 642 nm over the water background, of 3× the background and 5× the background respectively. This demonstrates the increase in sensitivity of fluorescence measurements over UV/VIS.

Example 6

Liposomes were prepared in water from a mixture of 10,12-tricosadiynoic acid (TRCDA) and dimyristoyl phosphatidylcholine (DMPC) in a 7:2 molar ratio. The liposomes were polymerized with 200 mJ/cm$^2$ of UV energy at 254 nm. Phospholipase A$_2$ (PLA$_2$) was dissolved in water at 1.0 mg/mL. A mixed buffer solution was prepared of TRIS (5 mM) and NaCl(150 mM) at pH 7.7 and combined with the PLA$_2$ solution at 9 parts buffer to 1 part PLA$_2$ solution. This solution was added to the liposome solution, diluting it to 0.091 mM in liposomes ("PLA$_2$ sample"), and the fluorescence monitored over one hour. A control solution of 9 parts mixed buffer to 1 part H$_2$O was also prepared. The control solution was used to dilute the liposome solution to 0.091 mM ("control solution") and the fluorescence emission at 635 nm monitored over one hour. Duplicate PLA$_2$ and control samples were prepared and the absorbance at 650 nm and 490 nm monitored and the 650 nm/490 nm absorbance ratio calculated at each time point.

The percentage change in the emission at 635 nm and the 650 nm/490 nm absorbance ratio were calculated as described in Example 4. After 5 minutes the emission of the PLA$_2$ solution had risen 42% while the control solution's emission had risen 14%. The absorbance ratio of the PLA$_2$ solution had dropped 29% while the ratio for the control had dropped 23%. After one hour the emission of the PLA$_2$ sample had risen 187%, the control sample emission had risen 130%; the absorbance ratio of the PLA$_2$ solution had dropped 56% while the control solution's absorbance ratio had dropped 44%.

Example 7

Liposomes were prepared in water from a mixture of 10,12-tricosadiynoic acid (TRCDA) and dimyristoyl phosphatidylcholine (DMPC) in a 7:2 molar ratio with the fluorophore BODIPY™ TR-Cadaverine incorporated at a ratio of 1 fluorophore:200 TRCDA. The liposomes were polymerized with 200 mJ/cm$^2$ of UV energy at 254 nm. Phospholipase A$_2$ (PLA$_2$) was dissolved in water at 1.0 mg/nL. A mixed buffer solution was prepared of TRIS (50 mM) and NaCl (150 mM) at pH 7.7 and combined with the PLA$_2$ solution at 9 parts buffer to 1 part PLA$_2$ solution. This solution was added to the liposome solution, diluting it to 0.091 mM in liposomes ("PLA$_2$ sample"), and the fluorescence monitored over one hour. A control solution of 9 parts mixed buffer to 1 part H$_2$O was also prepared. The control solution was used to dilute the liposome solution to 0.091 mM ("control solution:) and the fluorescence emission at 635 nm monitored over one hour. The percentage changes in the emission at 635 nm were calculated as described in Example 4. After 5 minutes the emission of the PLA$_2$ solution had risen 46% while the control solution's emission had risen 10%. After one hour the emission of the PLA$_2$ sample had risen 255% and the control sample emission had risen 152%.

Example 8

Liposome solutions were prepared from mixtures of 10,12-tricosadiynoic acid (TRCDA) and dimyristoyl phosphatidylcholine (DMPC) in a 7:2 molar ratio, with fluorophores added in a ratio of approximately 1 fluorophore:200 TRCDA. Each preparation had a different fluorophore added. The liposomes were polymerized with 40 mJ/cm$^2$ of UV energy at 254 nm. Phospholipase A$_2$ (PLA$_2$) was dissolved in water at 1.2 mg/mL. A mixed buffer solution was prepared of TRIS (894 mM), NaCl (150 mM) and CaCl$_2$ (4.5 mM) at pH 7.1 and combined with the PLA$_2$ solution at 9 parts buffer to 1 part PLA$_2$ solution. This solution was added to the liposome solutions, diluting them to 091 mM in liposomes, and the fluorescence of the liposomes at 630 nm monitored over one hour. A control solution was prepared that was 9 parts mixed buffer to 1 part H$_2$O. The control solution was used to dilute the liposome solution to 0.091 mM and the fluorescence of the liposomes monitored over one hour. A second control experiment consisted of diluting the liposome solutions to 0.091 mM with H$_2$O and monitoring the fluorescence over one hour. The data are presented in Table 3. It can be seen that the liposomes fluorescence increased for the samples exposed to PLA$_2$ and increased significantly less, or decreased for the samples exposed to the control buffer solution and to plain water.

TABLE 3

% Change in Liposome Fluorescence at 630 nm emission, at 1 h.

| Fluorophore | PLA$_2$/Buffer | H$_2$O/Buffer | H$_2$O |
|---|---|---|---|
| BODIPY™ 493/503 | 13% | −11% | −13% |
| Eu(THD)$_3$* | 24% | 6% | −1.5% |
| Tb(THD)$_3$* | 21% | 5% | −5% |

*THD = tris(2,2,6,6,-tetramethyl-3,5-heptadionate)

Example 9

Liposomes were prepared from 5,7-docosadiynoic acid with 5 molar % monosialoganglioside G$_{M1}$ and 0.5 molar % DIC-18(5) incorporated, 1 mM total lipid in H$_2$O, and photopolymerized under N$_2$ with 2.4J/cm$^2$. The liposome solution (20 μL) was combined with 10 mM sodium phosphate buffer at pH 6.25 (55 μM) in the wells of a 96-well microtiter plate. After 40 minutes either H$_2$O (25 μL); or 10 mM sodium phosphate buffer at pH 7.0 (25 μM); or cholera toxin B sub-unit (CTB)—0.74 mg/mL in 10 mM sodium phosphate buffer at pH 7.0 (25 μL), were added to each well. The fluorescence intensity at 680 nm was measured periodically over 4 hours. The wells with CTB showed an average increase of 193% in the fluorescence after 4 hours, the wells with buffer added showed an average increase of 129% and the wells with H$_2$O added showed an average change of −2%. A duplicate assay run with monitoring of the absorbance at 620 nm and 490 nm showed average changes in the 620 nm/490 nm absorbance ratios of −12% for CTB, −9% for buffer and −2% with H$_2$O.

Example 10

Liposomes were prepared from PDA with 0.5 molar/o DIC-18(5) incorporated. Anti-*chlamydia trachomatis* antibody halves, conjugated to 1,2-distearoyl-sn-glycero-3-phosphorylethanolaminocarproylmaleimide, were inserted via detergent dialysis using deoxycholate as described above. The liposomes were polymerized with 600 mJ/cm$^2$ to give polydiacetylene liposomes in the non-fluorescent form. The liposome solution (10 μL) was diluted with H$_2$O (80 μL) in a 96 well plate and *chlamydia trachomatis* elementary body solution (10$^8$/mL in 10 mM Na phosphate/154 mM NaCl at pH 7.4, 10 μL) was added. Buffer without elementary bodies was added to the control well. The samples were excited with 475 nm light and the fluorescence intensities at 635 nm (polydiacetylene emission) and 680 nm (fluorophore emission) were monitored. After 1 hour the fluorescence intensity at 635 nm was 3168 for the control and 3466 for the active sample; the fluorescence intensity at 680 nm was 2512 for the control and 3738 for the active sample.

Example 11

Figure 4:
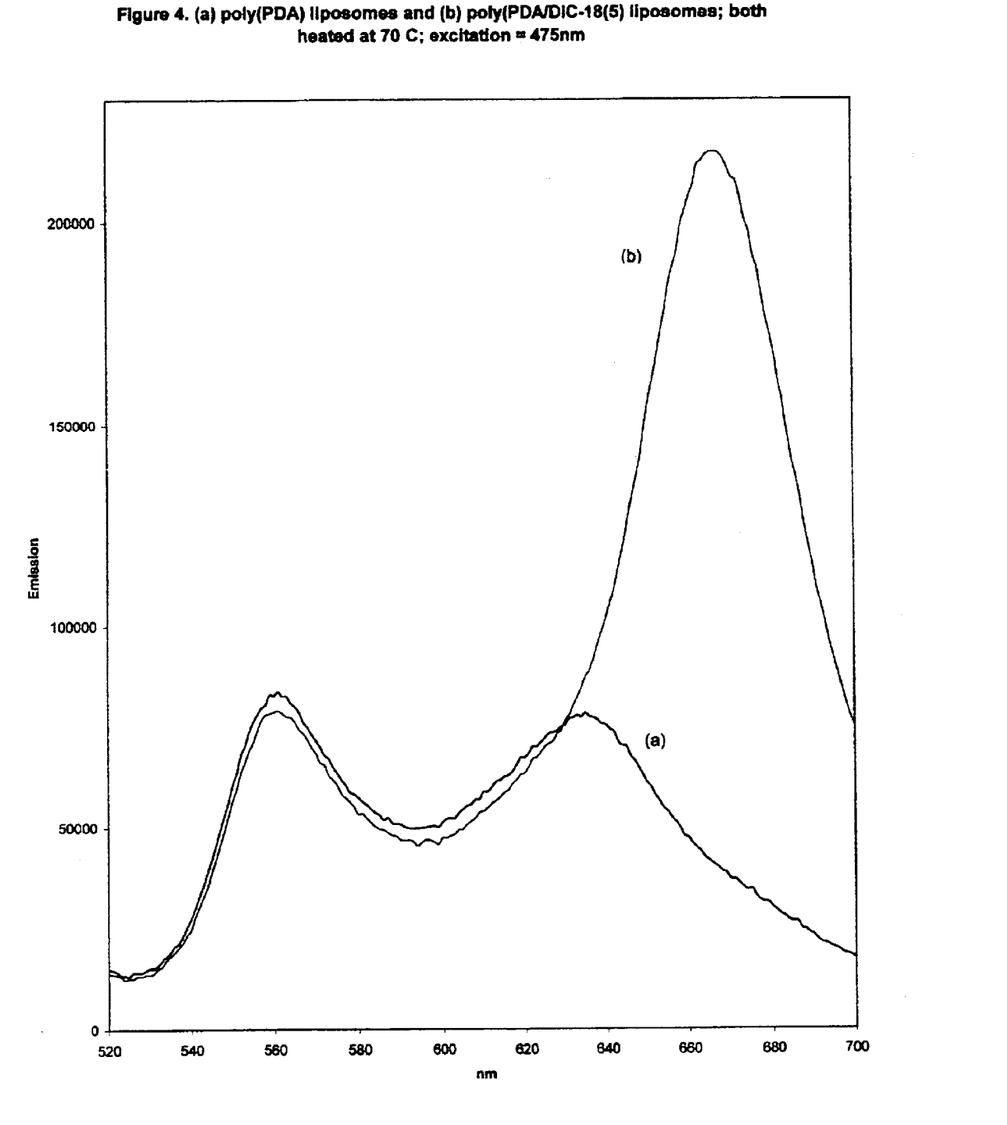
FIG. 4 illustrates the fluorescence of polydiacetylene liposomes with and without fluorophores incorporated.
Figure 5:
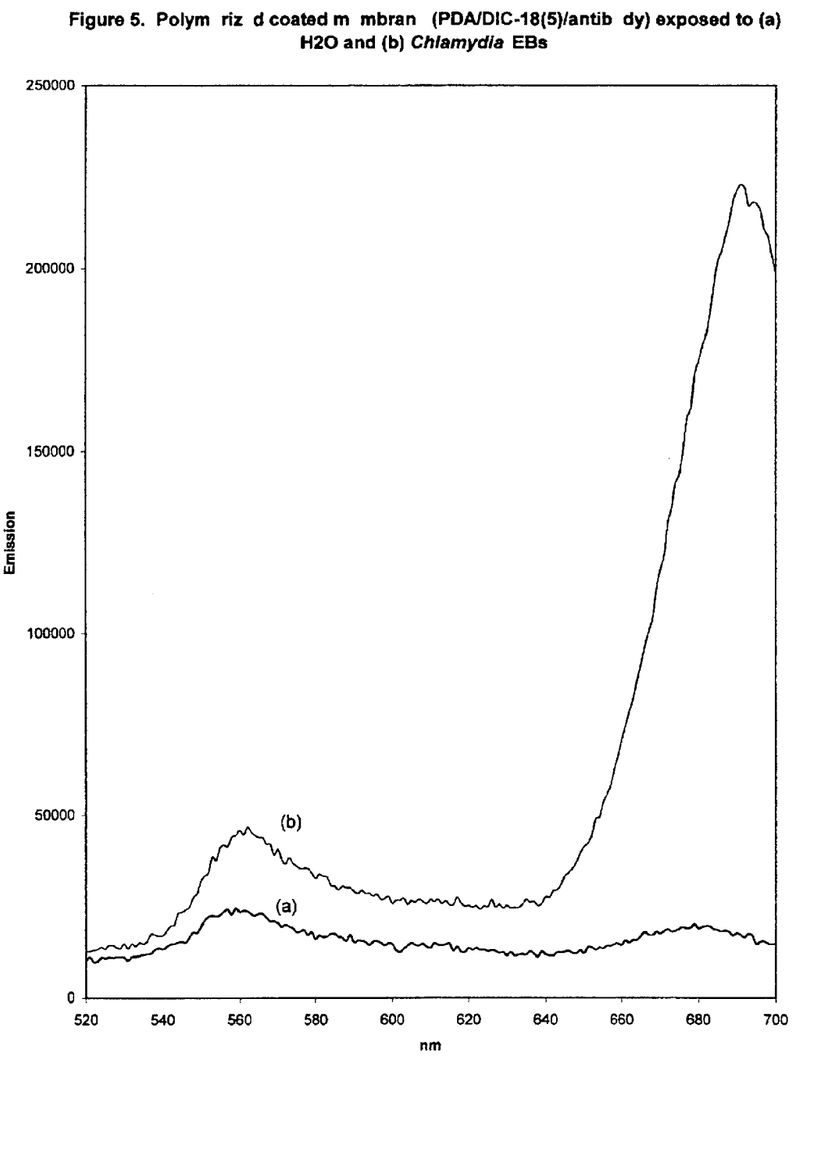
FIG. 5 illustrates the fluorescence spectra of a polydiacetylene array with fluorophores and anti-chlamydia antibodies incorporated, coated onto a nanoporous membrane, before and after exposure to chlamydia elementary bodies.

Unpolymerized TRCDA liposomes were prepared in water, chilled to 4° C. and the solution passed through a chilled hand-held extruder (Avestin Inc, Lipo-Fast Basic) fitted with a 100 nm pore polycarbonate membrane. The membrane was removed, chilled at 4° C. for 5 minutes, and then photopolymerized with 100 mJ/cm$^2$ of UV energy (254 nm). The membrane turned a deep blue, and retained the color over 2 months, stored in air and exposed to light. After 2 months the fluorescence of the membrane was read, the membrane was soaked in 25 mM NaHCO$_3$ for 1 minute, and the fluorescence read again—it had increased by 216% as shown in FIG. 4. Similar membranes have retained their original color and non-fluorescent state for over 12 months, and still could be converted to the fluorescent form.

Example 12

Liposomes were prepared from TRCDA, and anti-chlamydia antibodies conjugated to 1,2-distearoyl-sn-glycero-3-phosphorylethanolamino-carproylmaleimide were inserted as described above. The liposome solution was chilled at 4° C. for approximately 40 hours. Approximately 1.5 mL of the solution was taken up into a syringe, a syringe filter holder containing a 200 nm pore dark gray polycarbonate membrane (Poretics) was mounted on the syringe, and the solution filtered through the membrane to deposit the liposomes on/in the surface. The membrane was chilled briefly at −20° C. then exposed to 0.05 J/cm$^2$ of 254 nm UV light This produced a dark blue coating on the membrane.

The membrane was mounted on a black metal strip that was placed diagonally in a quartz cell (~2 mL volume). The cell was filled with solution (A) made of 1 part 10 mM sodium phosphates 54 mM NaCl pH 7.4 to 9 parts water.

The cell was placed in a holder with a 550 nm long pass filter mounted on the emission side in the Fluoromax 2 fluorometer. The sample was excited with 450 nm light and the emission at 615 nm measured every minute for one hour as a control experiment; no increase in the emission was seen. The emission was measured as S/R=the fluorescent signal divided by a reference signal taken directly from the excitation lamp; the reference value is less than 1 and compensates for fluctuations in the lamp intensity. The control solution was then removed and replaced with chlamydia elementary bodies (EBs) at ~$10^7$/mL in solution (A) without moving the quartz cell or sample. The sample was excited and the emission at 615 nm monitored as before for one hour and showed an increase. The sample then sat in the solution for 16 hours and the emission was measured again and showed further increase. After one hour in the control solution the sample's emission (SIR) was 99,556; after one hour in the buffer solution the sample's emission (S/R) was 112,472, and it was 123,928 after 16 hours.

Example 13

Liposomes were prepared from PDA with 0.5 molar % DIC-18(5) incorporated.

Anti-*chlamydia trachomatis* antibodies, conjugated to 1,2-distearoyl-sn-glycero-3-phosphorylethanolaminocarproylmaleimide, were inserted via detergent dialysis as described above. The liposomes were deposited on a white polycarbonate membrane with 100 nm pores as described in Example 12. The membrane was chilled at −20° C. and the coating photopolymerized with 0.08 J/cm$^2$ of UV energy at 254 nm. The membrane was mounted and exposed first to the control solution for one hour then to the EB solution as described in Experiment 12. The fluorescence emission (S/R) of the incorporated fluorophore was monitored at 676 nm (550 nm long pass filter): after one hour in the control solution it had changed −1%, while after one hour in the EB solution it had risen 63%, after 4 hours it had risen 332%.

Example 14

Liposomes were prepared from 5,7-tetracosadiynoic acid with 0.5 molaro DIC-18(5) incorporated. Anti-*chlamydia trachomatis* antibodies, conjugated to 1,2-distearoyl-sn-glycero-3-phosphorylethanolaminocarproylmaleimide, were inserted via detergent dialysis as described above. The liposomes were deposited on white polycarbonate membranes with 200 nm pores as described in Example 12;1 nil of unpolymerized liposome solution per 13 mm membrane. The membranes were chilled at −20° C. and the coatings photopolymerized with 0.20 J/cm$^2$ of UV energy at 254 nm.

Chlamydia elementary bodies (EBs) at ~$10^8$/mL in 10 mM Na phosphate/154 mM NaCl at pH 7.4, were diluted to $10_6$/mL with water. A comparable amount of the buffer was diluted similarly as a control solution. Two coated membranes were placed in syringe filter cartridges, each on top of a uncoated 200 nm pore polycarbonate membrane. The control solution (2 mL) was passed through one membrane and the EB solution (2 mL) through another, using a 3 mL plastic syringe to pressurize the liquid. Filtration took 15–20 minutes. The membranes were removed from the cartridges and mounted on black metal strips which were then placed in a quartz cell as described in Example 12. The fluorescence emission (550 nm long pass filter) was scanned for both samples and the fluorescence at 688 nm (coating fluorescence) was compared to the fluorescence at 560 nm (mostly background reflection): 688 nm/560 nm emission ratio was 0.60 for the membrane used to filter the EB solution and 0.49 for the membrane used to filter the control solution.

Further Examples

The following additional examples illustrate some further fluorescent detection systems according to the present invention:

Detection of cholera toxin or of cholera using poly(PDA) films with $G_{M1}$ ganglioside and diacetylenes with sialic acid head groups incorporated and with or without fluorophores in the films.

Detection of influenza virus with poly(PDA) liposomes with diacetylenes with sialic acid head groups incorporated and with or without fluorophores in the liposomes.

Detection of influenza virus with poly(PDA) films with diacetylenes with sialic acid head groups incorporated and with or without fluorophores in the films.

Detection of $PLA_2$ with poly(TRCDA) films with DMPC incorporated and with or without fluorophores in the films.

Detection of *Escherichia coli* with poly(TRCDA) liposomes with diactadecylglycerylether-β-gluocosides incorporated and with or without fluorophores in the liposomes.

Detection of *Escherichia coli*, with polydiacetylene liposomes with antibodies for *Escherichia coli*, incorporated and with or without fluorophores in the liposomes.

Detection of *Escherichia coli*, with poly(TRCDA) films with diactadecylglycerylether-β-gluocosides incorporated and with or without fluorophores in the films.

Detection of *Escherichia coli*, with polydiacetylene films with antibodies for *Escherichia coli*, incorporated and with or without fluorophores in the films.

Detection of Salmonella with polydiacetylene liposomes with antibodies for Salmonella incorporated and with or without fluorophores in the liposomes.

Detection of Salmonella with polydiacetylene films with antibodies for Salmonella incorporated and with or without fluorophores in the films.

Detection of Listeria with polydiacetylenc liposomes with antibodies for Listeria incorporated and with or without fluorophores in the liposomes.

Detection of Listeria with polydiacetylene films with antibodies for Listeria incorporated and with or without fluorophores in the films.

Detection of Campylobacter with polydiacetylene liposomes with antibodies for Campylobacter incorporated and with or without fluorophores in the liposomes.

Detection of Campylobacter with polydiacetylene films with antibodies for Campylobacter incorporated and with or without fluorophores in the films.

Detection of glucose with poly(N-hydroxysuccinimide PDA-PDA) films with hexokinase incorporated onto the surface and with or without fluorophores in the films.

Detection of glucose with poly(N-hydroxysuccinimide PDA-PDA) liposornes with hexokinase incorporated onto the surface and with or without fluorophores in the liposomes.

Detection of antigens with polydiacetylene liposomes with antibodies or antibody fragments incorporated, with or without fluorophores added to the liposomes.

Detection of antigens with polydiacetylene films with antibodies or antibody fragments incorporated, with or without fluorophores added to the films.

Detection of proteases including HIV protease with polydiacetylene liposomes with protease substrate incorporated with or without fluorophores added to the liposomes.

Detection of proteases including HIV protease with polydiacetylene films with protease substrate incorporated with or without fluorophores added to the films.

Detection of kinases including MAP kinases with polydiacetylene liposomes with kinase substrate incorporated with or without fluorophores added to the liposomes.

Detection of kinases including MAP kinases with polydiacetylene films with kinase substrate incorporated with or without fluorophores added to the films.

Detection of cholera toxin using poly(5,7-docosadiynoic acid) with $G_{M1}$ ganglioside incorporated, and with or without fluorophores coated onto a nanoporous membrane.

Detection of cholera toxin using poly(PDA) with $G_{M1}$ ganglioside and diacetylenes with sialic acid head groups incorporated, and with or without fluorophores coated onto a nanoporous membrane.

Detection of influenza virus with poly(PDA with diacetylenes with sialic acid head groups incorporated) and with or without fluorophores coated onto a nanoporous membrane.

Detection of $PLA_2$ with poly(TRCDA) with DMPC incorporated and with or without fluorophores coated onto a nanoporous membrane.

Detection of *Escherichia coli*, with poly(TRCDA) with diactadecylglycerylether-β-gluocosides incorporated and with or without fluorophores coated onto a nanoporous membrane.

Detection of *Escherichia coli*, with polydiacetylene with antibodies for *Escherichia coli*, incorporated and with or without fluorophores coated onto a nanoporous membrane.

Detection of Salmonella with polydiacetylene with antibodies for Salmonella incorporated and with or without fluorophores coated onto a nanoporous membrane.

Detection of Listeria with polydiacetylene with antibodies for Listeria incorporated and with or without fluorophores coated onto a nanoporous membrane.

Detection of Catnpylobacter with polydiacetylene with antibodies for Campylobacter incorporated and with or without fluorophores coated into a nanoporous membrane.

Detection of glucose with poly(N-hydroxysuccinimide PDA-PDA) with hexokinase incorporated onto the surface and with or without fluorophores coated onto a nanoporous membrane.

Detection of antigens with polydiacetylene with antibodies or antibody fragments incorporated, with or without fluorophores coated onto a nanoporous membrane.

Detection of proteases including HIV protease with polydiacetylene with protease substrate incorporated with or without fluorophores coated onto a nanoporous membrane.

Detection of kinases including MAP kinases with polydiacetylene with kinase substrate incorporated with or without fluorophores coated onto a nanoporous membrane.

Detection of antibodies or antibody fragments with polydiacetylene arrays with the appropriate antigen or epitope incorporated, with or without fluorophores incorporated.

Detection of antibodies or antibody fragments with polydiacetylene liposomes with the appropriate antigen or epitope incorporated, with or without fluorophores incorporated.

Detection of antibodies or antibody fragments with polydiacetylene films with the appropriate antigen or epitope incorporated, with or without fluorophores incorporated.

Detection of antibodies or antibody fragments with polydiacetylene arrays with the appropriate antigen or epitope incorporated, with or without fluorophores, coated onto a nanoporous membrane.

Detection of antibodies or antibody fragments with polydiacetylene liposomes with the appropriate antigen or epitope incorporated, with or without fluorophores, coated onto a nanoporous membrane.

Detection of antibodies or antibody fragments with polydiacetylene films with the appropriate antigen or epitope incorporated, with or without fluorophores, coated onto a nanoporous membrane.

Detection of nucleic acids with polydiacetylene arrays with nucleic acids incorporated, with or without fluorophores incorporated.

Detection of nucleic acids with polydiacetylene liposomes with nucleic acids incorporated, with or without fluorophores incorporated.

Detection of nucleic acids with polydiacetylene films with nucleic acids incorporated, with or without fluorophores incorporated.

Detection of nucleic acids with polydiacetylene with nucleic acids incorporated, with or without fluorophores incorporated, coated onto a nanoporous membrane.

Detection of proteins with polydiacetylene arrays with nucleic acids incorporated, with or without fluorophores incorporated.

Detection of proteins with polydiacetylene liposomes with nucleic acids incorporated, with or without fluorophores incorporated.

Detection of proteins with polydiacetylene films with nucleic acids incorporated, with or without fluorophores incorporated.

Detection of proteins with polydiacetylene with nucleic acids incorporated, with or without fluorophores incorporated, coated onto a nanoporous membrane.

Detection of nucleic acids with polydiacetylene arrays with proteins incorporated, with or without fluorophores incorporated.

Detection of nucleic acids with polydiacetylene liposomes with proteins incorporated, with or without fluorophores incorporated.

Detection of nucleic acids with polydiacetylene films with proteins incorporated, with or without fluorophores incorporated.

Detection of nucleic acids with polydiacetylene with proteins incorporated, with or without fluorophores incorporated, coated onto a nanoporous membrane.

Detection of proteins with polydiacetylene arrays with proteins incorporated, with or without fluorophores incorporated.

Detection of proteins with polydiacetylene liposomes with proteins incorporated, with or without fluorophores incorporated.

Detection of proteins with polydiacetylene films with proteins incorporated, with or without fluorophores incorporated.

Detection of proteins with polydiacetylene, with proteins incorporated, with or without fluorophores incorporated, coated onto a nanoporous membrane.

What is claimed is:

1. A method for the detection of an analyte in a sample, which comprises contacting the sample to be tested with a three-dimensional array comprising a polydiacetylene backbone and a substrate, wherein the substrate has direct affinity for an analyte or is capable of binding to an analyte or is capable of reacting with an analyte; and wherein a change, if any, in fluorescence of said polydiacetylene backbone is in response to analyte present in said sample;

and detecting the change in fluorescence to indicate the presence of an analyte.

2. The method of claim 1 wherein the array is in the form of a solution of liposomes or tubules.

3. The method of claim 1 wherein the analyte is an enzyme and the substrate is a reactive substrate of that enzyme.

4. The method of claim 1 or 2 wherein the analyte is an antigen and the substrate is the antibody of that antigen.

5. The method of claim 1 or 2 wherein the analyte is an antigen and the substrate is a fragment of the antibody of that antigen.

6. The method of claim 1 or 2 wherein the analyte is an antibody or antibody fragment and the substrate is the antigen of that antibody.

7. The method of claim 1 or 2, wherein the analyte is an antibody or antibody fragment and the substrate is the epitope of that antibody.

8. The method of claim 2 wherein the analyte is an enzyme and the substrate is a reactive substrate of that enzyme.

9. The method of claim 1 wherein the polydiacetylene of the array is in the non-fluorescent form, exhibiting a fluorescent signal that is about 1–3 times that of the background and less than that of the corresponding fluorescent form.

10. The method of claim 1 wherein the substrate includes a ligand.

11. The method of claim 10 wherein the array is in the form of a solution of a liposome or tubule.

12. The method of claim 1 wherein the substrate includes a reactive substrate.

13. The method of claim 12 wherein the array is in the form of a solution of a liposome or tubule.

14. The method of any one of claims 1 to 13 wherein the three-dimensional array further comprises a fluorophore and wherein the change in fluorescence of the polydiacetylene array is monitored.

15. The method of any one of claims 1 to 13 wherein the three-dimensional array further comprises a fluorophore and wherein the change in fluorescence of the fluorophore is monitored.

16. The method of claim 1 wherein the array does not contain a further fluorophore.

17. The method of claim 1 wherein the change in fluorescence is detected by exposure to light having wavelengths below 550 nm and measurement of the emission.

18. The method of claim 1 wherein the change in fluorescence is detected by exposure to light having wavelengths between 450 and 500 nm and measurement of the emission.

19. The method of claim 1 wherein the polydiacetylene of the array exhibits fluorescence and the fluorescence increases as an indication of the presence of the analyte.

* * * * *

UNITED STATES PATENT AND TRADEMARK OFFICE
CERTIFICATE OF CORRECTION

| | |
|---|---|
| PATENT NO. | : 6,984,528 B2 |
| APPLICATION NO. | : 09/811538 |
| DATED | : January 10, 2006 |
| INVENTOR(S) | : Reppy et al. |

Page 1 of 1

It is certified that error appears in the above-identified patent and that said Letters Patent is hereby corrected as shown below:

On the title page,

[*] Notice: Subject to any disclaimer, the term of this patent is extended or adjusted under 35 USC 154(b) by (287) days Delete the phrase "by 287 days" and insert -- by 407 days--

Signed and Sealed this

First Day of May, 2007

JON W. DUDAS
*Director of the United States Patent and Trademark Office*